US008152746B2

(12) United States Patent
Nan

(10) Patent No.: US 8,152,746 B2
(45) Date of Patent: Apr. 10, 2012

(54) POWERED MASSAGER WITH COAXIAL ACTUATORS

(75) Inventor: Simon Siu Man Nan, Ontario (CA)

(73) Assignee: Nanma Manufacturing Co., Ltd. (HK)

(*) Notice: Subject to any disclaimer, the term of this patent is extended or adjusted under 35 U.S.C. 154(b) by 824 days.

(21) Appl. No.: 12/266,857

(22) Filed: Nov. 7, 2008

(65) Prior Publication Data

US 2010/0121234 A1 May 13, 2010

(51) Int. Cl.
*A61H 1/00* (2006.01)
*A61F 5/00* (2006.01)

(52) U.S. Cl. .......... 601/46; 600/38

(58) Field of Classification Search .......... 601/46, 601/48, 68–70, 72, 73, 78, 80; 600/38
See application file for complete search history.

(56) References Cited

U.S. PATENT DOCUMENTS

| | | | | |
|---|---|---|---|---|
| 5,399,820 A * | 3/1995 | Silfvast | 200/314 |
| 6,028,531 A * | 2/2000 | Wanderlich | 340/7.6 |
| 6,190,307 B1 * | 2/2001 | Tsai | 600/38 |
| 7,717,867 B2 * | 5/2010 | Nan | 601/46 |
| 2006/0063929 A1 * | 3/2006 | Otera et al. | 544/91 |
| 2006/0069330 A1 * | 3/2006 | Nan | 601/72 |
| 2007/0142754 A1 * | 6/2007 | Nan | 601/70 |
| 2011/0034837 A1 * | 2/2011 | Lee | 601/46 |

* cited by examiner

*Primary Examiner* — Kristen Matter
(74) *Attorney, Agent, or Firm* — Polsinelli Shughart PC

(57) ABSTRACT

A powered massager having coaxially mounted first and second massage actuators that are positioned along the main axis of the powered massager is disclosed. The powered massager further includes a hand-held unit including a control panel for controlling the operation of the massager and a power source that is operatively associated with an electric motor that drives a rotatable output shaft through a gear arrangement. In one embodiment, the first massage actuator is a squirming massage actuator having a plurality of frames interposed between rolling members that are operable when the output shaft is driven by the electric motor, while the second massage actuator is a vibratory massage actuator that is operatively associated with the power source through a conductive pathway established between the power source and the vibratory massage actuator.

13 Claims, 5 Drawing Sheets

POWERED MASSAGER WITH COAXIAL ACTUATORS

FIELD

This document relates to a powered massager, and in particular to a powered massager with coaxially mounted massage actuators.

BACKGROUND

Powered massagers are known in the art for providing a massaging effect to the user. In particular, a powered massager in the form of sexual aid device may have several massage actuators mounted to a single device with one massage actuator being applied to one area of the body while the other massage actuator is applied to another area of the body. In some instances, the user may desire to insert the sexual aid device inside a single body cavity such that both massage actuators are simultaneously applied to the same area of the body at the same time. However, prior sexual aid devices have positioned these multiple massage actuators along different axes of the device in order for a single device to accommodate more than one massage actuator due to the difficulty of structurally and operationally mounting more than one massage actuator along the same axis. A typical prior art sexual aid device may have an elongated tubular main body with one massage actuator disposed along the main axis of the body, while the other massage actuator is disposed along a secondary branch extending from the main body at an axis different from the main axis of the device. Unfortunately, this bifurcated configuration of the massage actuators mounted along different axes of the device prevents the user from being able to apply both massage actuators simultaneously to the same area of the body, such as inside the same body cavity of the user.

Therefore, there is a need in the art for a powered massager having more than one massage actuator mounted along the same axis of the device.

SUMMARY

In one embodiment, a powered massager may include a hand-held unit including a casing containing a power source and having a control panel for controlling the operation of the powered massager. The first massage actuator may be coaxially mounted to the casing for providing a first massage action and a second massage actuator coaxially mounted to the first massage actuator for providing a second massage action, wherein the first and second massage actuators are coaxially mounted along the same axis of the powered massager.

In another embodiment, a powered massager may include a hand-held unit including a casing containing a power source and having a control panel for controlling the operation of the powered massager. The power source may be operatively associated with an electric motor adapted to rotate an output shaft through a gear box arrangement. A squirming massage actuator may be coaxially mounted to the casing for providing a first massage action with the squirming massage actuator including a plurality of frames operatively engaged to the output shaft. Each of the plurality of frames may have at least one pivoting support arrangement for a plurality of pivoting rolling members. In addition, a vibratory massage actuator may be coaxially mounted to the squirming massage actuator for providing a second massage action, wherein the squirming massage actuator and the vibratory massage actuator are coaxially mounted to one another along the main axis of the powered massager.

In yet another embodiment, a powered massager may include a hand-held unit including a casing containing a power source and having a control panel for controlling the operation of the powered massager. The power source may be operatively associated with an electric motor adapted to rotate an output shaft through a gear box arrangement. A squirming massage actuator may be coaxially mounted to the casing for providing a squirming massage action with the squirming massage actuator including a plurality of frames operatively engaged to the output shaft, wherein each of the plurality of frames having at least one pivoting support arrangement for a respective plurality of pivoting rolling members. A vibratory massage actuator may be coaxially mounted to the squirming massage actuator for providing a vibratory massage action, wherein the vibratory massage actuator includes a body defining a cavity adapted to receive a vibratory component, wherein the vibratory massage actuator includes one or more conductive rings in operative association with a biased pin and rivet arrangement. The engagement of the biased pin with the rivet establishes power between the one or more conductive rings and the power source. The squirming massage actuator and the vibratory massage actuator may be coaxially mounted to one another along the same longitudinal axis of the powered massager.

Additional objectives, advantages and novel features will be set forth in the description which follows or will become apparent to those skilled in the art upon examination of the drawings and detailed description which follows.

BRIEF DESCRIPTION OF THE DRAWINGS

Corresponding reference characters indicate corresponding elements among the view of the drawings. The headings used in the figures should not be interpreted to limit the scope of the claims.

DETAILED DESCRIPTION

Figure 1:
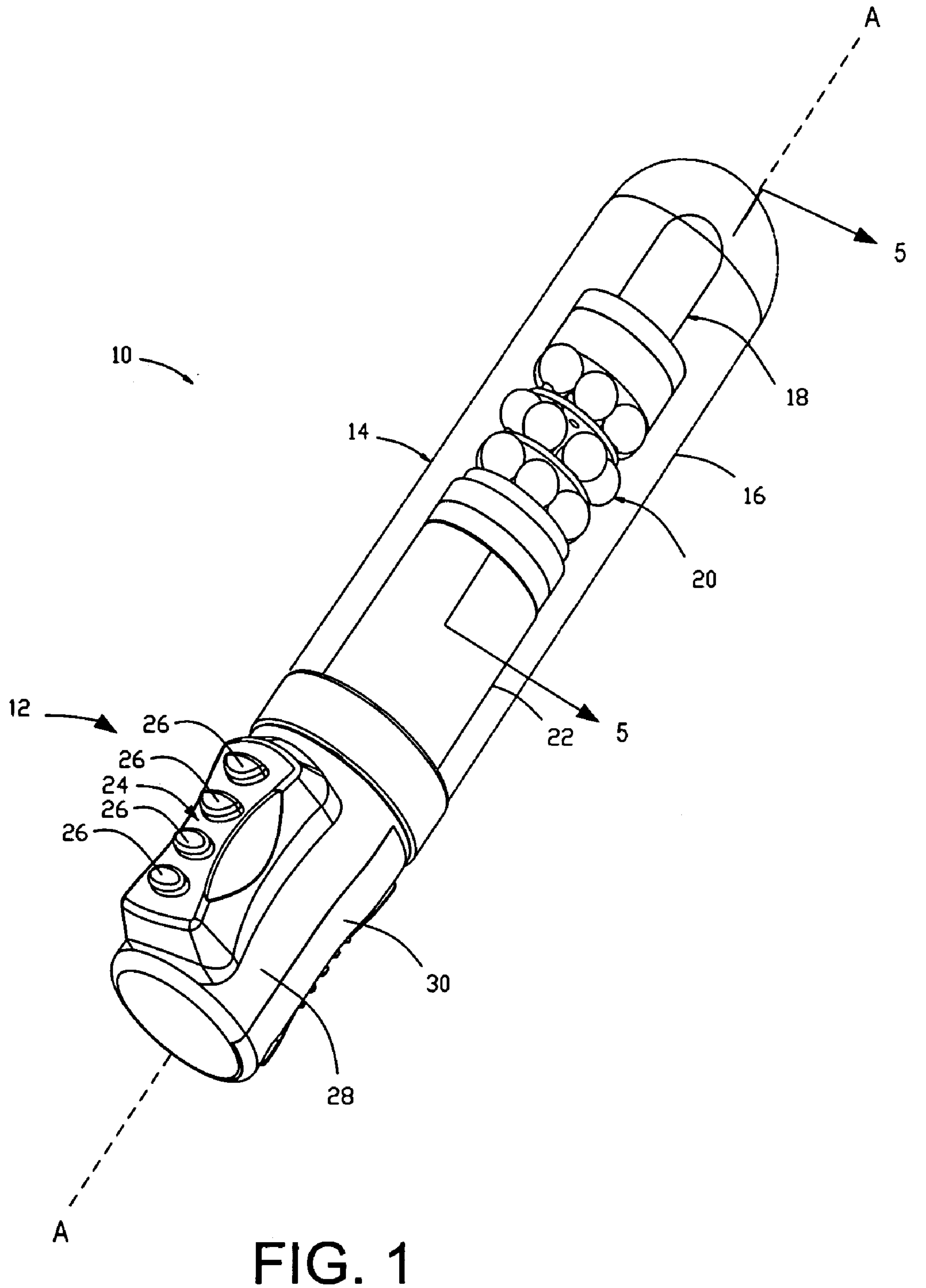
FIG. 1 is an elevated perspective view of the powered massager.
Figure 4:
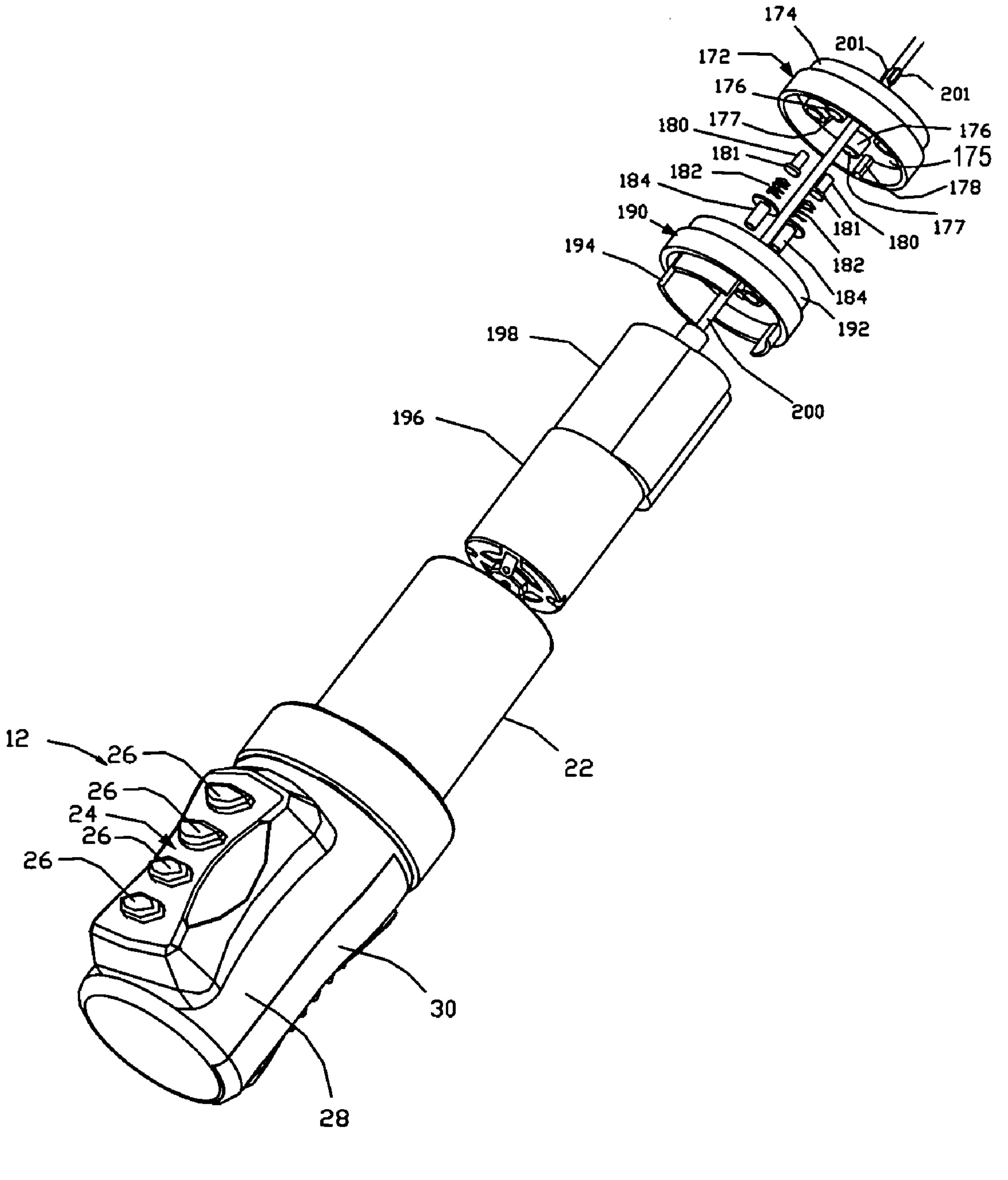
FIG. 4 is an isolated exploded view of the powered massager showing the casing, gear housing, electric motor and gear box.

Referring to the drawings, an embodiment of the powered massager is illustrated and generally indicated as 10 in FIG. 1. As shown, the powered massager 10 includes a hand-held unit 12 that has a control panel 24 having a plurality of control buttons 26 for controlling the various massage functions of a massage actuation unit 14 having co-axially mounted massage actuators. The hand-held unit 12 includes a casing 28 having a battery cover 30 in communication with one or more batteries (not shown) disposed inside the casing 28 that provide electric power to the massage actuation unit 14. In one embodiment, the massage actuation unit 14 may include a vibratory massage actuator 18 coaxially mounted to a squirming massage actuator 20, although other types of massage actuators are contemplated. Referring to FIGS. 1 and 4, the control panel 24 may operate the squirming massage actuator

20 through an electric motor 196 that drives a gear box 198 that are collectively disposed inside a gear housing 22 attached to the hand-held unit 12. As shown, the vibratory massage actuator 18 and the squirming massage actuator 20 may be coaxially mounted along a longitudinal main axis A of the power massager 10. As used herein, the term "proximal" shall mean the side or portion of the powered massager 10 that faces the casing 28, while the term "distal" shall mean the side or portion of the powered massager 10 that faces away from the casing 28.

In one embodiment, the vibratory massage actuator 18 and the squirming massage actuator 20 may be disposed inside a flexible outer sleeve 16 that is adapted for transmitting to the user the respective massage effects generated by operation of the vibratory massage actuator 18 and squirming massage actuator 20. In one embodiment, the flexible outer sleeve 16 may have a generally tubular configuration with a rounded distal portion, although in other embodiments the flexible outer sleeve 16 may have different shapes, such as different phallic configurations.

Figure 2:
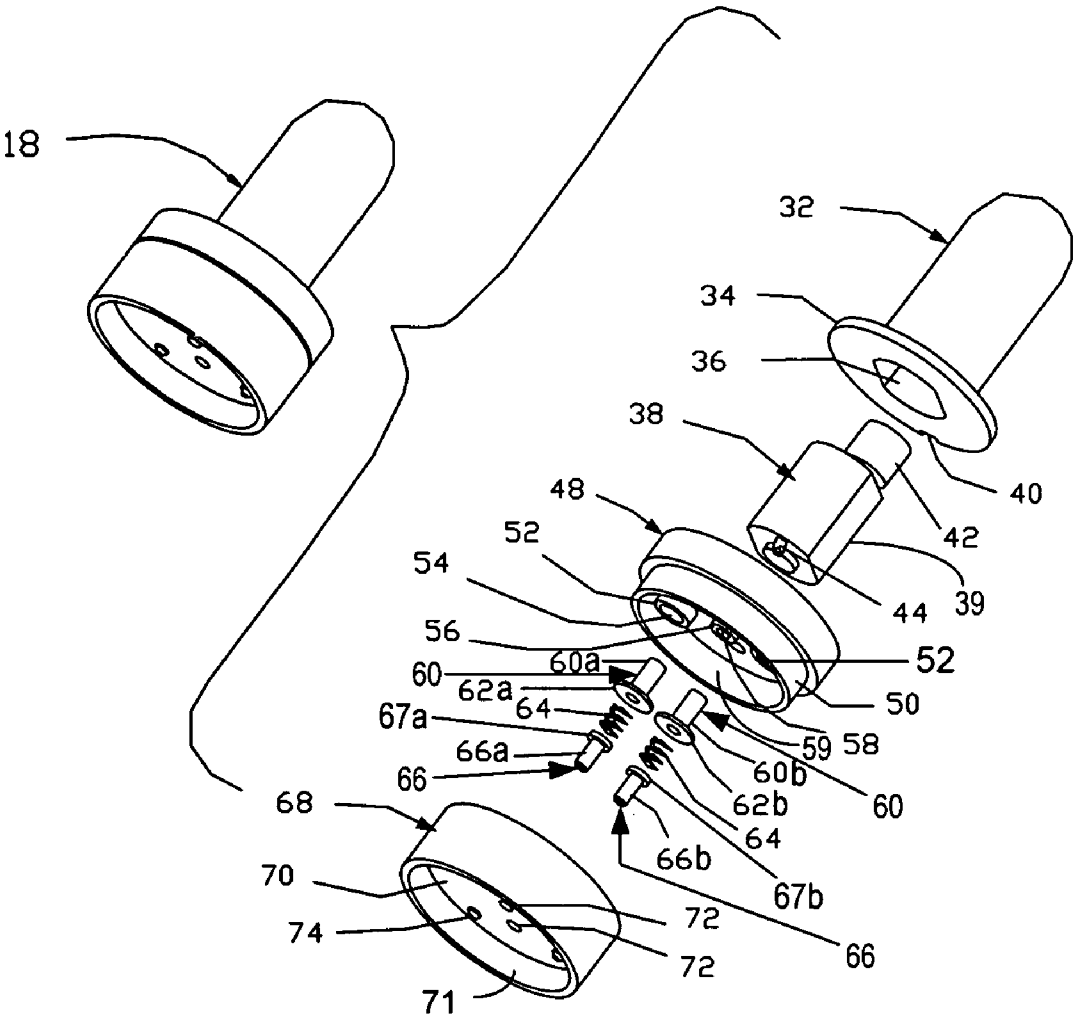
FIG. 2 is an exploded view of a vibratory massage actuator of the powered massager.

Referring to FIG. 2, the vibratory massage actuator 18 generates vibratory and/or pulsating massage effect. In one embodiment, the vibratory massage actuator 18 may include a pole cover 48 engaged to hollow cap 32 and a pole box 68. The hollow cap 32 defines a center cavity 36 in communication with a flange 34 with the circumferential edge of the flange 34 defining a slot 40 adapted for engagement with an inward protrusion (not shown) defined inside the pole cover 48 when engaging the pole cover 48 to the hollow cap 32. The vibratory massage actuator 18 further includes a vibratory component 38 disposed inside the center cavity 36 of the hollow cap 32 for generating the vibratory or pulsating massage effects. The vibratory component 38 includes an electric motor 39 having a rotating rod (not shown) that spins an eccentric mass 42 such that the vibratory and/or pulsating effect is transmitted through the hollow cap 32. The electric motor 39 further includes a pair of electrodes 44 that provide electrical power to the electric motor 39. During assembly, the electric motor 39 is disposed inside the center cavity 36 of the hollow cap 32 and may be bonded or otherwise secured to the distal end of the pole cover 48 to form one unit during assembly.

The pole cover 48 may define a circular step portion 50 along its external circumference and a recess 59 along its proximal end. The recess 59 of pole cover 48 communicates with a pair of bosses 52 with each boss 52 defining a through-hole 54 for accommodating a respective metal pin 66 and rivet 60. In one embodiment, metal pins 66 may be a pair of metal pins 66*a* and 66*b* used to establish a conductive pathway with a pair of metal rivets 60, such as metal rivets 60*a* and 60*b*. As such, each metal pin 66*a* and 66*b* is operatively associated with a respective rivet head 62*a* and 62*b* of metal rivets 60*a* and 60*b*, respectively, through respective spring 64 for establishing a conductive pathway between the power source and the electrodes 44 of the electric motor 39 to actuate the vibratory component 38. Once the electric motor 39 of vibratory component 38 and the hollow cap 32 are assembled with the pole cover 48, each of the electrodes 44 is operatively associated with respective rivets 60*a* and 60*b* to provide electrical power to the electric motor 39. The recess 59 of the pole cover 48 further communicates with a center boss 56 defining a center through-hole 58.

Figure 5:
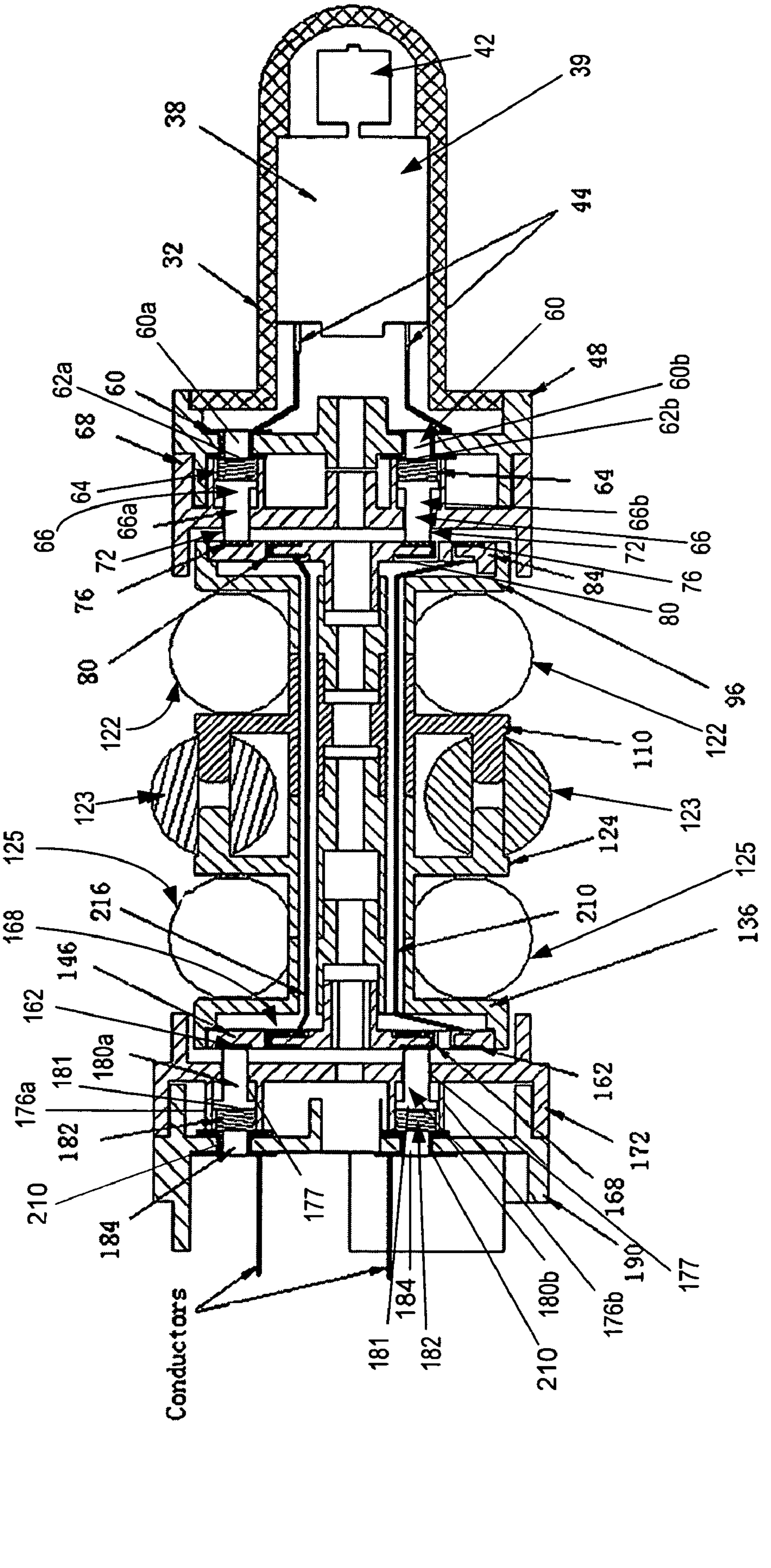
FIG. 5 is a cross-sectional view of the powered massager taken along line 5-5 of FIG. 1.

As shown in FIGS. 2 and 5, the proximal portion of the pole cover 48 is engaged to the pole box 68 when assembling the vibratory massage actuator 18. The pole box 68 includes a distal recess (not shown) on one side and a proximal recess 71 on the opposite side thereof defining a bottom face 70 that includes a pair of stepped holes (not shown) defining through-holes 72 which communicate with both proximal and distal recesses of the pole box 68. As noted above, the pair of metal springs 64 may be disposed within the distal recess of the pole box 68 that are operatively engaged to a respective pair of metal pins 66*a* and 66*b* respective through-holes 72. When assembled, the springs 64 become compressed and the distal ends of the metal springs 64 become biased against and operatively associated with respective rivet heads 62*a* and 62*b* of metal rivets 60*a* and 60*b*, respectively, while the opposite proximal end of the metal springs 64 are biased against and operatively associated with respective pin heads 67*a* and 67*b* of metal pins 66*a* and 66*b*, respectively. In operation, the compressed springs 64 may apply a bias against respective pin heads 66*a* and 66*b* that axially slide within respective through-holes 72 towards operative engagement with respective conductive rings 76 and 80 such that pin 66*a* contacts conductive ring 76 and pin 66*b* contacts conductive ring 80. A pair of knobs 74 may protrude from the bottom face 70 of the proximal recess 71. After the powered massager 10 is assembled, the proximal end of the metal pins 66 will protrude from the bottom face 70 to a height approximately the same as the knobs 74.

Figure 3:
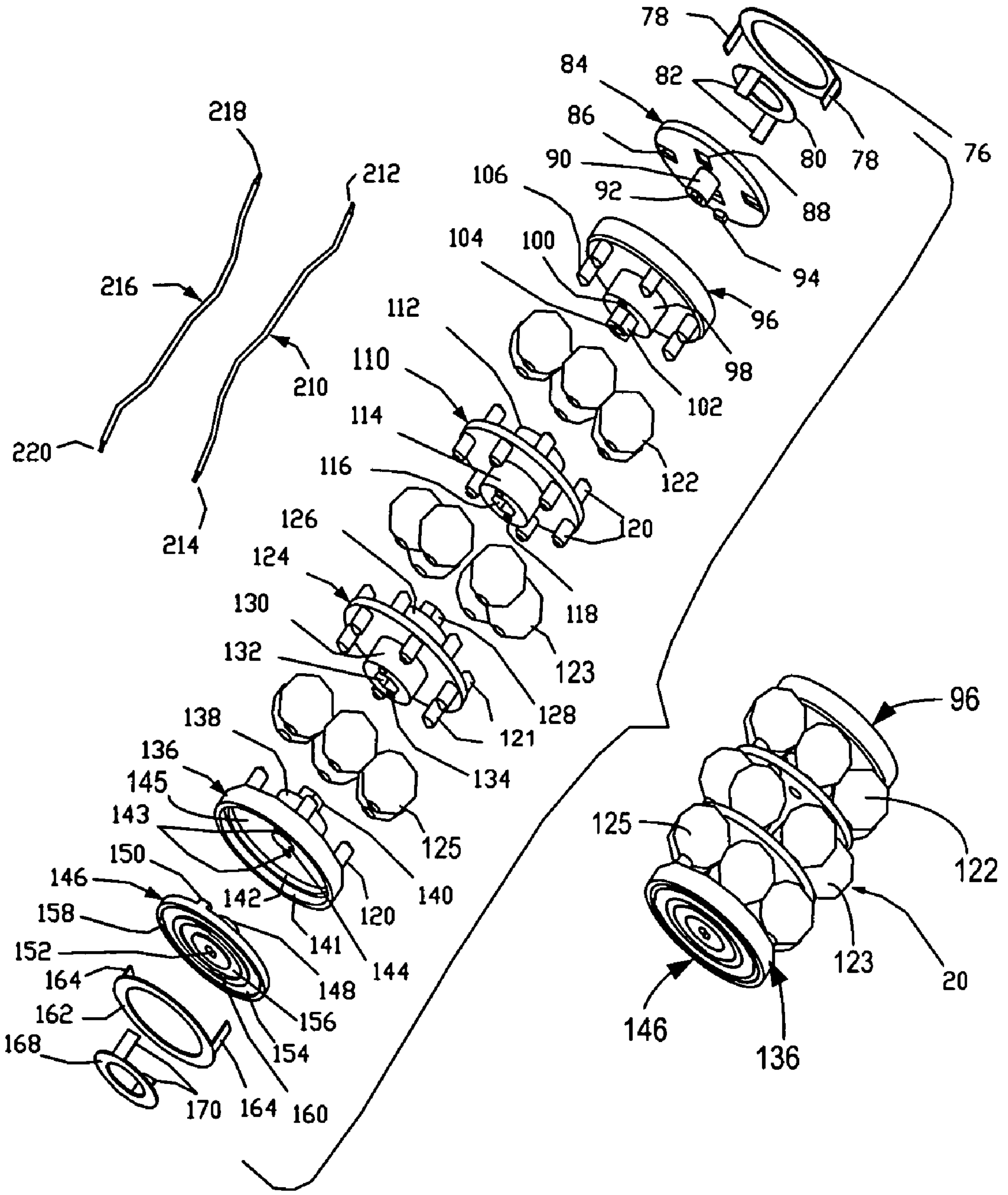
FIG. 3 is an exploded view of a squirming massage actuator of the powered massager.

Referring to FIG. 3, the squirming massage actuator 20 is coaxially mounted to the gear box 198 below the vibratory massage actuator 18. In one embodiment, the squirming massage actuator 20 may include a body collectively comprising an uppermost frame 96, upper intermediate frame 110, lower intermediate frame 124 and lowermost frame 136. The uppermost frame 96 defines a distal recess (not shown) adapted to engage a ring-mounting frame 84 therein. The ring-mounting frame 84 defines a pair of concentric distal recessions (not shown) for accommodating conductive rings 76 and 80, respectively. The conductive ring 76 may include a pair of tabs 78 that form a portion of the conductive pathway that provides electrical power from the power source to the vibratory massage actuator 18 through the squirming massage actuator 20. The conductive ring 80 may have an outer diameter that is smaller than the inner diameter of the conductive ring 76 and includes a pair of tabs 82 that also form a portion of the conductive pathway. The distal recession of the ring-mounting frame 84 that accommodates conductive ring 76 defines a pair of through-holes 86 that are sized and shaped to receive respective tabs 78 which are inserted therein and then bent to retain the conductive ring 80 in position. Similarly, at the other distal recession of ring-mounting frame 84 are defined a pair of through-holes 88 that are adapted to receive respective tabs 82 of the conductive ring 80 which are inserted therein and bent during assembly for retaining the conductive ring 80 in position. Once the conductive rings 76, 80 are engaged to the ring-mounting frame 84, a conductive end 212 of an electric wire 210 may be soldered to one of the tabs 78 of conductive ring 76, while the conductive end 218 of an electric wire 216 may be soldered to one of the tabs 82 of conductive ring 80. The electric wires 210 and 216 establish a portion of the conductive pathway adapted to provide electrical power between the power source and the vibratory massage actuator 18.

The uppermost frame 96 of the squirming massage actuator 20 may define a distal recess (not shown) for accommodating the ring-mounting frame 84. As shown, the proximal portion of the ring-mounting frame 84 includes a center boss 90 that defines a through-hole 92 as well as a protrusion 94 that extends outwardly near the edge of the frame 84. The protrusion 94 is adapted to engage a slot (not shown) defined along the bottom face of the distal recess of the uppermost frame 96 when engaging the ring-mounting frame 84 to the uppermost frame 96.

At the proximal end of the uppermost frame 96, a center block 98 is defined that includes a center hole (not shown) at the distal end of the frame 96 for accommodating the center boss 90 of the ring-mounting frame 84. The center block 98 includes a hexagonal boss 102 that extends axially from the block 98 and defines a center hole 104. In addition, a pair of through-holes 100 may be defined along the center block 98 near the hexagonal boss 102 that receive electric wires 210 and 216. The uppermost frame 96 further includes a plurality of posts 106 circumferentially distributed along the proximal face of the frame 96 in order to provide a pivoting support arrangement for a plurality of rolling members 122.

The upper intermediate frame 110 of the squirming massage actuator 20 may include a center block 112 that defines a hexagonal center hole (not shown) adapted for engagement with the hexagonal boss 102 of uppermost frame 96. In addition, the upper intermediate frame 110 includes a center block 114 that defines a center hexagonal hole 116 for engagement with a hexagonal boss 128 of lower intermediate frame 124. The center blocks 112, 114 each define a pair of through-holes 118 adapted for receiving the electric wires 210, 216. A plurality of posts 120 may also be circumferentially distributed on the distal and proximal sides of the upper intermediate frame 110 to form a pivoting support arrangement for rolling members 122 and 123, respectively.

The lower intermediate frame 124 of the squirming massage actuator 20 may include a center block 126 on the distal side having a hexagonal boss 128 for engagement with the hexagonal hole 116 of the upper intermediate frame 110 when engaging frame 110 to frame 124. The proximal side of the lower intermediate frame 124 may include a center block 130 having a hexagonal hole 132 for engagement with a hexagonal boss 140 of the lowermost frame 136. Similar to frames 96 and 110, blocks 126 and 130 of the lower intermediate frame 124 define a pair of through-holes 134 adapted to receive electric wires 210 and 216. In addition, the proximal side of the lower intermediate frame 124 includes a plurality of posts 121 circumferentially distributed on the distal and proximal sides of frame 124 to provide a pivoting support arrangement for the rolling members 123 and 125, respectively.

The lowermost frame 136 of the squirming massage actuator 20 may include a center block 138 on its distal side having a hexagonal boss 140 for engagement with the hexagonal hole 132 of the lower intermediate frame 124 when engaging frame 136 to frame 124. A recess 145 may be defined along the proximal side of the lowermost frame 136 that communicates with first and second shoulders 141 and 142. The first shoulder 141 may be sized and shaped to accommodate a ring-mounting frame 146 therein, while the second shoulder 142 may define a slot (not shown) adapted for engagement with a protrusion 150 of the ring-mounting frame 146 when engaging the lowermost frame 136 to the ring-mounting frame 146. In addition, the lowermost frame 136 may define a pair of through-holes 143 adapted to receive electric wires 210 and 216. As further shown, the center block 138 of the lowermost frame 136 may define a center hole 144 adapted for engagement with a circular boss 148 of ring-mounting frame 146 when engaging frame 136 to frame 146.

The ring-mounting frame 146 of the squirming massage actuator 20 may define first and second concentric recessions 154 and 156 sized and shaped for accommodating first and second conductive rings 162 and 168, respectively. In addition, the distal portion of the ring-mounting frame 146 includes a center boss 148 that may communicate with a center through-hole 152 sized and shaped for accommodating protrusions 201 of output shaft 200. As shown, the first conductive ring 162 includes a pair of opposing tabs 164, while the second conductive ring 168 also includes a pair of opposing tabs 170. The first concentric recession may define a pair of through-holes 158 adapted to receive tabs 164 such that the free end of tabs 164 may be bent for retaining the first conductive ring 162 in position within recession 154. Similarly, the second concentric recession 156 may define a pair of through-holes 160 adapted to receive tabs 170 such that the free ends of tabs 170 may be bent during assembly to retain the second conductive ring 168 in position within recession 156.

After the first and second conductive rings 162 and 168 are engaged within the first and second concentric recessions 154 and 156, the conductive end 214 of electric wire 210 may be inserted through one of the pair of through-holes 143 and then soldered onto one of the tabs 164, while the conductive end 220 of electric wire 216 may be inserted through the other through-hole 143 and then soldered onto one of the tabs 170. Once so assembled, the conductive ring 76 is conductively connected to the conductive ring 162 through electric wire 210, while conductive ring 80 is conductively connected to conductive ring 168 through electric wire 216. In this arrangement, a conductive pathway is established between the proximal end and the distal end of the power source and the squirming massage actuator 20, respectively.

Referring to FIG. 4, a lower pole cover 172 and a lower pole box 190 are collectively positioned between the squirming massage actuator 20 and the gear housing 22 of the powered massager 10. The lower pole cover 172 may define a stepped circular portion 174, while the proximal side of cover 172 may define a recess 175 that communicates with a pair of bosses 176. Each boss 176 may define a stepped hole 177 having a larger circular section sized and shaped to accommodate an arrangement of a metal pin 180 and metal spring 182 that forms a portion of the conductive pathway. As shown in FIG. 5, boss **176*a* defines a stepped hole 177 for accommodating the metal pin 180*a* and metal spring 182, while boss 176*b* is adapted for accommodating the metal pin 180*b* and metal spring 180**.

Referring back to FIG. 4, the lower pole cover 172 may define a protrusion 178 positioned within the recess 175 that is adapted to engage a slot (not shown) defined along the circular portion 192 of the lower pole box 190 when engaging the cover 172 to box 190. The lower pole box 190 may include a plurality of segmented circular portions 194 that extends axially outward from the proximal side of box 190.

As shown in FIGS. 4 and 5, metal rivets 184 may be inserted into through-holes (210) defined along the recess of lower pole box 190. The cover 172 may then be engaged to the circular portion 192 of the pole box 190. In this arrangement, the proximal end of the springs 182 are operatively engaged to a respective metal rivet 184, while the distal end of the springs 182 are operatively engaged to a respective metal pin 181. As shown, a metal pins **180*a* and 180*b* extend outwardly from the bottom face (not shown) of the distal recess of cover 172. In operation, the compressed state of the springs 182 apply a bias against the respective metal pins 180 disposed within through-holes 177 such that metal pin 180*a* is brought into contact with conductive ring 162 and metal pin 180*b* is brought into contact with conductive ring 168 such that the squirming massage actuator 20** may receive electrical power.

Referring to FIGS. 1, 3 and 4, gear box 198 may be operatively engaged to output shaft 200 for mechanically driving the squirming massage actuator 20 when made operational by the control panel 24. The electric motor 196 rotates the output shaft 200 via gear box 198 for actuating the squirming action generated by the squirming massage actuator 20. In one embodiment, the outer sleeve 16 may be engaged to the hand-held unit 12 such that the vibratory massage actuator 18, squirming massage actuator 20 and gear housing 22 are fully encased inside the outer sleeve 16. As discussed above, the output shaft 200 includes a pair of knob-like protrusions 201 which are adapted to engage respective center hole 152 of ring-mounting frame 146 such that there is no relative angular rotation between the output shaft 200 and the squirming massage actuator 20. As a result, when the electric motor 196 rotates the output shaft 200 through gear box 198, torque is generated through the ring-mounting frame 146 and the lowermost frame 136 that is then imparted to the other frames 124, 110, and 96 of the squirming massage actuator 20 to generate the squirming action.

During operation of the powered massager 10, the output shaft 200 rotates such that there is a relative rotation established between the proximal end of the squirming massage actuator 20, e.g., ring-mounting frame 146, and the lower pole cover 172, thereby causing the metal pins 180*a* and 180*b* to be biased by respective springs 182 and contact conductive rings 162 and 168, respectively, thereby establishing a conductive pathway between the power source and the squirming massage actuator 20. Similarly, at the distal end of the output shaft 200, the same relative rotation is established between the distal end of the squirming massage actuator 20 and the vibratory massage actuator 18, thereby causing the springs 64 to bias respective pins 66*a* and 66*b* to be brought into contact respective conductive rings 76 and 80, thereby establishing a conductive pathway between the power source and the vibratory massage actuator 18. As such, this arrangement that establishes the conductive pathway permits electric power to be delivered from the hand-held unit 12 to the vibratory massage actuator 18 despite the structural movement of the interrelating components and frames of the squirming massage actuator 20 that are physically interposed between the hand-held unit 12 and vibratory massage actuator 18.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A powered massager comprising:

a hand-held unit including a casing containing a power source and having a control panel for controlling the operation of the powered massager, a first massage actuator coaxially mounted to the casing for providing a first massage action, and a second massage actuator coaxially mounted to the first massage actuator for providing a second massage action, wherein the first and second massage actuators are coaxially mounted along the same main axis of the powered massager, wherein the power source is in operative association with a conductive pathway for providing electrical power to the first and second massage actuators, the conductive pathway having one or more conductive rings being in operative association with a respective biased in for providing electrical power to the first and second massage actuators, wherein the movement of the first massage actuator relative to the second massage actuator causes each respective pin to be biased and brought into operative engagement with the one or more conductive rings to provide electrical power to the second massage actuator.

2. The powered massager of claim 1, wherein the power source is in operative association with an electric motor that drives a rotatable output shaft through a gear box encased in a gear housing mounted to the hand-held unit.

3. The powered massager of claim 2, wherein the rotatable output shaft drives the first massage actuator such that the first massage actuator moves relative to the second massage actuator.

4. The powered massager of claim 2, wherein the conductive pathway is established between the power source and the second massage actuator when the first massage actuator moves relative to the second massage actuator.

5. The powered massager of claim 2, wherein the first massage actuator comprises a plurality of frames that move relative to one another during operation of the rotatable output shaft, wherein the conductive pathway to the second massage actuator is established when at least one of the plurality of frames of the first massage actuator moves relative to the second massage actuator.

6. The powered massager of claim 5, wherein the conductive pathway includes a respective spring in operative association with each biased pin that is in operative engagement with the one or more conductive rings such that the movement of at least one of the plurality of frames causes each spring to bias its respective biased pin to be brought into contact with the one or more conductive rings.

7. The powered massager of claim 1, wherein the same main axis is the longitudinal axis of the hand-held unit.

8. A powered massager comprising:

a hand-held unit including a casing containing a power source with the power source being operatively associated with an electric motor adapted to rotate an output shaft through a gear-box arrangement, a squirming massage actuator coaxially mounted to the casing for providing a first massage action, the squirming massage actuator including a plurality of frames operatively engaged to the output shaft, each of the plurality of frames having at least one pivoting support arrangement for a plurality of pivoting rolling members, and a vibratory massage actuator coaxially mounted to the squirming massage actuator for providing a second massage action, wherein the squirming massage actuator and the vibratory massage actuator are coaxially mounted to one another along the main axis of the powered massager, wherein the vibratory massage actuator includes a pole cover having one or more pins with each of the one or more pins being in operative association with a respective spring for establishing a conductive pathway between the power source and the vibratory massage actuator when the output shaft is made operable, wherein each spring applies a bias to the one or more pins by the action of the output shaft which establishes a conductive pathway between the power source and the vibratory massage actuator, and wherein terminating operation of the output shaft causes disengagement between the one or more pins and a respective conductive ring and breaking of the conductive pathway between the power source and the vibratory massage actuator.

9. The powered massager of claim 8, wherein the vibratory massage actuator is disposed inside a cavity defined by hollow cap engaged to a pole cover.

10. The powered massager of claim 8, wherein each spring applies a bias to the one or more pins by rotative action of the output shaft that causes relative movement of the squirming massage actuator relative to the vibratory massage actuator that establishes the conductive pathway between the power source and the vibratory massage actuator, while terminating operation of the output shaft causes the squirming massage actuator to be become stationary relative to the vibratory massage actuator and disengage the one or more pins from the conductive ring.

11. The powered massager of claim 10, wherein the output shaft is operatively engaged to one or more of the plurality of frames of the first massage actuator for moving the first massage actuator relative to the second massage actuator which is stationary.

12. The powered massager of claim 8, wherein each respective spring applies a bias when the output shaft is operable, and wherein each respective spring does not apply a bias when the operation of the output shaft is terminated.

13. A powered massager comprising:

a hand-held unit including a casing containing a power source and having a control panel for controlling the operation of the powered massager, the power source being operatively associated with an electric motor adapted to rotate an output shaft through a gear-box arrangement, a squirming massage actuator coaxially mounted to the casing for providing a squirming massage action, the squirming massage actuator including a plurality of frames operatively engaged to the output shaft, wherein each of the plurality of frames having at least one pivoting support arrangement for a respective plurality of pivoting rolling members, and a vibratory massage actuator coaxially mounted to the squirming massage actuator for providing a vibratory massage action, wherein the vibratory massage actuator includes a body defining a cavity adapted to receive a vibratory component, wherein the vibratory massage actuator includes one or more conductive rings in operative association with a biased pin and a rivet in operative association with the biased pin wherein operation of the output shaft causes the biased pin to engage the rivet and establish a conductive pathway between the one or more conductive rings and the power source, wherein the squirming massage actuator and the vibratory massage actuator are coaxially mounted to one another along the same longitudinal axis of the powered massager.

* * * * *

UNITED STATES PATENT AND TRADEMARK OFFICE

CERTIFICATE OF CORRECTION

PATENT NO. : 8,152,746 B2
APPLICATION NO. : 12/266857
DATED : April 10, 2012
INVENTOR(S) : Simon Siu Man Nan It is certified that error appears in the above-identified patent and that said Letters Patent is hereby corrected as shown below:

In the Claims

Col. 7, line 64 (claim 1, line 16): “in” should read --pin--

Col. 8, line 12 (claim 4, line 1): “claim 2” should read --claim 3--

Col. 9, line 16 (claim 12, line 1): “claim 8” should read --claim 11--

Signed and Sealed this
Twenty-third Day of July, 2013

Teresa Stanek Rea
*Acting Director of the United States Patent and Trademark Office*